(12) United States Patent
Peng et al.

(10) Patent No.: US 10,352,878 B2
(45) Date of Patent: Jul. 16, 2019

(54) REAR-PROJECTION PHOTODETECTION YARN CLEARING APPARATUS AND ULTRAVIOLET ENHANCED SILICON PHOTODIODE THEREOF

(71) Applicant: Shanghai Institute of Kehua Optoelectronic Techniques, Shanghai (CN)

(72) Inventors: Hejian Peng, Shanghai (CN); Zuoliang Wu, Shanghai (CN)

(73) Assignee: Shanghai Institute of Kehua Optoelectronic Techniques, Shanghai (CN)

( * ) Notice: Subject to any disclaimer, the term of this patent is extended or adjusted under 35 U.S.C. 154(b) by 41 days.

(21) Appl. No.: 15/871,875

(22) Filed: Jan. 15, 2018

(65) Prior Publication Data

US 2019/0072498 A1    Mar. 7, 2019

(30) Foreign Application Priority Data

Sep. 7, 2017  (CN) .......................... 2017 1 0800255

(51) Int. Cl.
| | |
|---|---|
| G01N 21/84 | (2006.01) |
| G01N 21/952 | (2006.01) |
| H01L 31/02 | (2006.01) |
| H01L 31/0232 | (2014.01) |
| H01L 31/0288 | (2006.01) |
| H01L 31/103 | (2006.01) |

(Continued)

(52) U.S. Cl.
CPC ......... *G01N 21/952* (2013.01); *B65H 63/065* (2013.01); *H01L 31/02019* (2013.01); *H01L 31/0288* (2013.01); *H01L 31/02325* (2013.01); *H01L 31/103* (2013.01); *H01L 31/173* (2013.01); *H01L 31/1804* (2013.01); *H01L 31/1864* (2013.01); *G01N 2021/8444* (2013.01)

(58) Field of Classification Search
CPC .......... G01N 2021/8444; G01N 21/952; H01L 31/02019; H01L 31/02325; H01L 31/0288; H01L 31/103; H01L 31/173; H01L 31/1864
USPC .................................................. 356/429–431
See application file for complete search history.

(56) References Cited

U.S. PATENT DOCUMENTS

| | | | |
|---|---|---|---|
| 2007/0090394 A1* | 4/2007 | Bui ..................... | H01L 27/1446 257/127 |
| 2010/0032710 A1* | 2/2010 | Bui ..................... | H01L 27/1446 257/127 |

(Continued)

*Primary Examiner* — Sunghee Y Gray
(74) *Attorney, Agent, or Firm* — Gokalp Bayramoglu

(57) ABSTRACT

A rear-projection photodetection yarn clearing apparatus includes a light emitting diode and a detector arranged behind a to-be-detected yarn, and further includes a reflector arranged in front of the to-be-detected yarn. A front end face of the light emitting diode is flush with a photosurface of the detector, a light filter for capturing light rays having a waveband from 330 nm to 470 nm is also arranged in front of the light emitting diode and the detector, and a light-reflecting surface of the reflector is in parallel with the photosurface of the detector. The light emitting diode includes an ultraviolet light emitting diode, and the detector includes an ultraviolet enhanced silicon photodiode. The ultraviolet enhanced silicon photodiode is made from a high-resistivity N-type (111) silicon wafer having a resistivity of 3,000 Ω·cm and a field oxide thickness of 1,000 nm.

11 Claims, 3 Drawing Sheets

(51) Int. Cl.
*H01L 31/173* (2006.01)
*H01L 31/18* (2006.01)
*B65H 63/06* (2006.01)

(56) References Cited

U.S. PATENT DOCUMENTS

2017/0098730 A1* 4/2017 Mazzillo ......... H01L 31/022416
2017/0207256 A1* 7/2017 Sugawa ............... H01L 27/144
2018/0047858 A1* 2/2018 Aso .................... H01L 21/0455
2018/0202859 A1* 7/2018 Mazzillo ................ G01J 1/429

* cited by examiner

REAR-PROJECTION PHOTODETECTION YARN CLEARING APPARATUS AND ULTRAVIOLET ENHANCED SILICON PHOTODIODE THEREOF

FIELD OF TECHNOLOGY

The present disclosure relates to a rear-projection photodetection yarn clearing apparatus and an ultraviolet enhanced silicon photodiode thereof.

BACKGROUND

To improve quality of textiles, it is required to detect hetero fibre and different heterogeneous colors in homogeneous fibre, which is collectively referred to as yarn clearing. In the world today, widely-used yarn clearing methods include a photodetection method, a capacitive detection method, and a detection method combining both.

Principles of the photodetection method are as shown in FIG. 1, including a light emitting diode 1, a yarn 2, and a detector 3 sequentially arranged. The light emitting diode directly irradiates on the to-be-detected yarn, the yarn blocks a part of light emitted from the light emitting diode, and the detector inspects the quality of the yarn by detecting variation of luminous flux blocked. In this method, the variation of the luminous flux blocked by the yarn is used as an assessment variable. Hence, generally only those quality problems having a negative effect on the sectional area of the yarn can be detected, for example, slubs and neps of the yarn, short and thick, long and thick, long and thin. But this method is unable to detect hetero fibre or homogeneous heterochromous fibre.

Some foreign electronic yarn clearers adopt the method combining the photodetection and the capacitive detection. This method can detect hetero fibre and homochromatic fibre, but is complex in design and high in cost.

SUMMARY

An objective of the present disclosure is to provide a rear-projection photodetection yarn clearing apparatus to solve the technical problem that in the prior art it is impossible to detect hetero fibre and homogeneous heterochromous fibre using a photodetection yarn clearing apparatus. Another objective of the present disclosure is further to provide an ultraviolet enhanced silicon photodiode used in the rear-projection photodetection yarn clearing apparatus.

To implement the above objectives, the rear-projection photodetection yarn clearing apparatus of the present disclosure adopts the following technical solutions.

A rear-projection photodetection yarn clearing apparatus includes a light emitting diode and a detector arranged behind a to-be-detected yarn, and further includes a reflector arranged in front of the to-be-detected yarn. A front end face of the light emitting diode is flush with a photosurface of the detector, a light filter for capturing light rays having a waveband from 330 nm to 470 nm is also arranged in front of the light emitting diode and the detector, and a light-reflecting surface of the reflector is in parallel with the photosurface of the detector. The light emitting diode includes an ultraviolet light emitting diode, and the detector includes an ultraviolet enhanced silicon photodiode. The ultraviolet enhanced silicon photodiode is made from a high-resistivity N-type (111) silicon wafer having a resistivity of 3,000Ω·cm and a field oxide thickness of 1,000 nm. A side of the silicon wafer is implanted with boron having an implantation dose of $4\times10^{14}$ cm$^{-2}$~$5\times10^{14}$ cm$^{-2}$ and energy of 30 Kev to form a P-type area, and another side of the silicon wafer is implanted with phosphorus having an implantation dose of $5\times10^{15}$ cm$^{-2}$ and energy of 100 Kev to form an N+ area. The P-type area of the silicon wafer is polished, the N+ area of the silicon wafer is burnished, and both the P-type area and the N+ area have an oxide layer thickness of 50 nm~60 nm.

The ultraviolet enhanced silicon photodiode is processed using a two-stage high and low temperature annealing process: first processed at a high temperature of 1,000° C. for 30 s, and then processed at a low temperature of 600° C. for 8-12 h.

The light emitting diode is symmetrically arranged at a left side and a right side of the detector, the number of the light emitting diodes at either side is at least two, and the light emitting diodes at either side are uniformly distributed at intervals along upper and lower directions.

A shell of the light emitting diode includes a frosting surface diverging light rays.

The detector is connected to a signal processing system, which includes a signal receiving module, an amplifier module, a filter module, a shaper module and a comparison output module sequentially arranged.

The ultraviolet enhanced silicon photodiode of the present disclosure adopts the following technical solution.

An ultraviolet enhanced silicon photodiode is made from a high-resistivity N-type (111) silicon wafer having a resistivity of 3,000Ω·cm and a field oxide thickness of 1,000 nm. A side of the silicon wafer is implanted with boron having an implantation dose of $4\times10^{14}$ cm$^{-2}$~$5\times10^{14}$ cm$^{-2}$ and energy of 30 Kev to form a P-type area, and another side of the silicon wafer is implanted with phosphorus having an implantation dose of $5\times10^{15}$ cm$^{-2}$ and energy of 100 Kev to form an N+ area. The P-type area of the silicon wafer is polished, the N+ area of the silicon wafer is burnished, and both the P-type area and the N+ area have an oxide layer thickness of 50 nm~60 nm.

The ultraviolet enhanced silicon photodiode is processed using a two-stage high and low temperature annealing process: first processed at a high temperature of 1,000° C. for 30 s, and then processed at a low temperature of 600° C. for 8-12 h.

Beneficial effects of the present disclosure are as below: in the rear-projection photodetection yarn clearing apparatus of the present disclosure, the front end of the light emitting diode is flush with the photosurface of the detector, so that light emitted from the light emitting diode does not directly enter into the detector but is filtered by the light filter, irradiates the to-be-detected yarn, and then is reflected by the to-be-detected yarn or the reflector back to the photosurface of the detector, which is advantageous to reducing impact of stray light on a detection result and enhancing a signal to noise ratio of a captured signal. However, a special ultraviolet enhanced silicon photodiode can begin to respond at a lower waveband, and can generate larger photocurrent intensity. Therefore, the ultraviolet enhanced silicon photodiode of the present disclosure has high light wave capture rate and photocurrent conversion rate. As a consequence, it is possible to detect homogeneous heterochromous fibre and homochromatic hetero fibre in the to-be-detected yarn only using the photodetection method.

Further, the shell of the light emitting diode includes a frosting surface, allowing light rays emitted from the light emitting diode to be diverged by the frosting surface and then to uniformly irradiate the to-be-detected yarn through the light filter, which is advantageous to enhancing a degree of uniformity of each portion of the to-be-detected yarn in receiving light intensity and increasing a probability of determining the homogeneous heterochromous fibre and the homochromatic hetero fibre.

DESCRIPTION OF THE EMBODIMENTS

Figure 1:
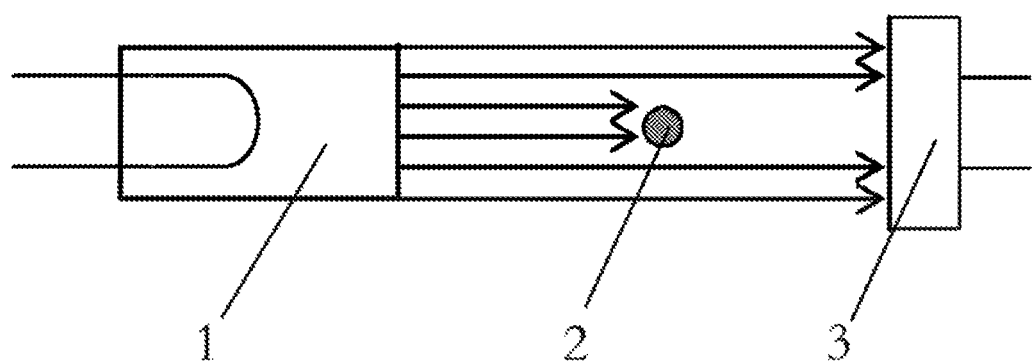
FIG. 1 is a schematic diagram of a photodetection yarn clearing apparatus.
Figure 2:
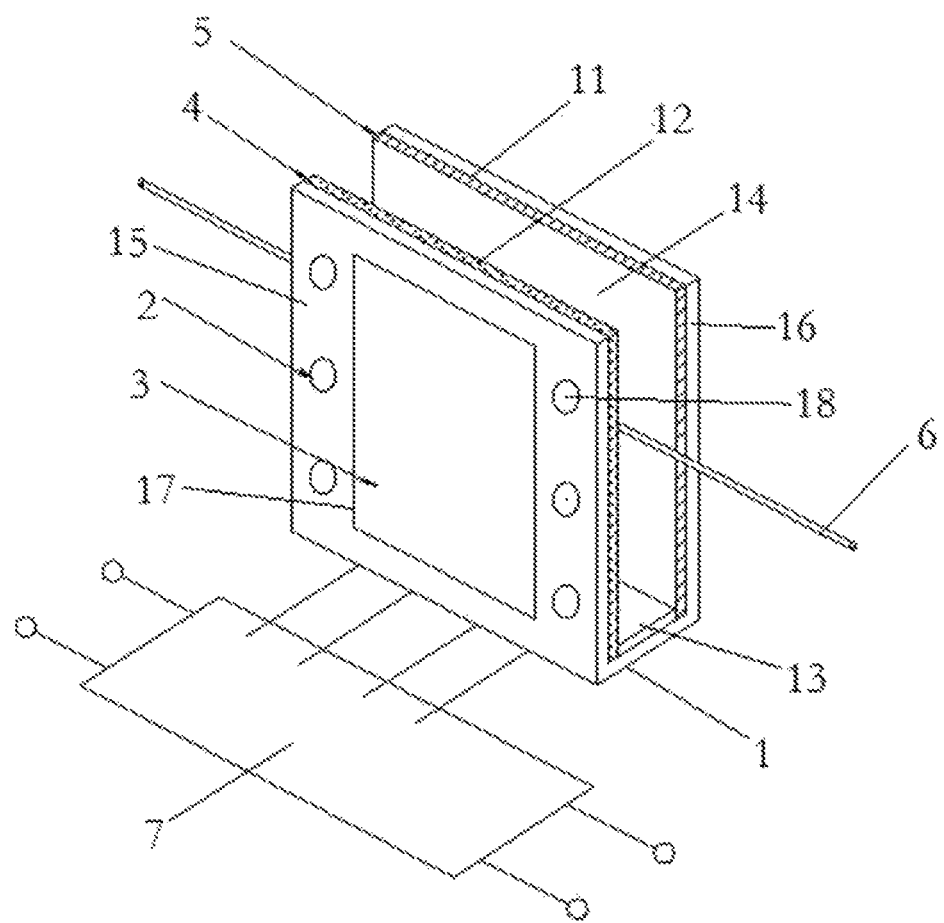
FIG. 2 is a schematic structural diagram of a rear-projection photodetection yarn clearing apparatus according to an embodiment of the present disclosure.

An embodiment of the rear-projection photodetection yarn clearing apparatus of the present disclosure:

FIG. 2 shows a specific structure of the rear-projection photodetection yarn clearing apparatus of the present disclosure, which includes a bracket 1. The bracket 1 includes a first interior side 11 positioned in front, a second interior side 12 positioned in the rear, and a third interior side 13 positioned beneath. The first interior side 11, the second interior side 12 and the third interior side 13 cause the bracket 1 to be concave. A concave-shaped middle cavity 14 allows a to-be-detected yarn 6 to pass through along a left direction and a right direction. The bracket 1 is separated by the middle cavity 14 into a front bracket 15 and a rear bracket 16.

A cross section of the rear bracket 16 is shaped like a rectangle, and a middle portion of the rear bracket 16 is provided with a rectangular through hole 17 which is front-back penetrated through, where the through hole 17 has a left-right width of 6.45 mm and a height of 6.2 mm, and the through hole 17 is internally provided with a detector 3. On the rear bracket 16, a left end and a right end of the through hole 17 are respectively provided with three mounting holes 18 for mounting a light emitting diode 2. The three mounting holes 18 at either side are uniformly distributed at intervals along upper and lower directions, and the mounting holes 18 at the left side and the right side of the rear bracket 16 are bilaterally symmetrical. In other embodiments, the left side and the right side of the rear bracket may be respectively provided with two or more light emitting diodes 2. The more the light emitting diodes 2 are, the more uniform the emitted light rays are. To ensure the light rays emitted from the light emitting diode 2 are more uniform, a shell surface of the light emitting diode 2 is a frosting surface, so that light rays emitted from the shell inside are diverged by the frosting surface and then uniformly irradiate into the middle cavity 14.

The light emitting diode 2 is an ultraviolet light emitting diode that can emit light rays having a wavelength ranging from 340 nm to 405 nm. A front end of the light emitting diode 2 and of the detector 3 does not go beyond the second interior side 12. The second interior side 12 is provided with a light filter 4 for filtering heterochromatic light out and only allowing light rays whose wavelength ranges from 330 nm to 470 nm to pass through. The first interior side 11 is provided with a reflector 5.

After irradiating on the to-be-detected yarn 6 in the middle cavity 14, ultraviolet light may be reflected back by the reflector 5. Light rays reflected back irradiate on the photosurface of the detector 3 through the light filter. The detector 3 converts a received light signal into a weak electrical signal. After the electrical signal is processed by a signal processing system 7, a control signal may be emitted to switch off hetero homochromatic fibre and homogeneous heterochromous fibre in the to-be-detected yarn 6.

The signal processing system 7 includes a signal receiving module 71, an amplifier module 72, a filter module 73, a shaper module 74, and a comparison output module 75. The signal receiving module 71 includes a current amplifier, and forms a main amplifying circuit together with the amplifier module 72. The main amplifying circuit only amplifies instead of shaping or processing the waveform of the received signal so as to avoid having a negative effect on restorability of the signal. The filter module 73 is configured to restore a heterochromatic signal portion in the signal and demodulate change of the heterochromatic signal. Therefore, after the light signal received by the detector 3 is amplified, filtered, shaped and compared, a detection signal may be outputted, which may indicate whether the to-be-detected yarn 6 includes homochromatic hetero fibre or homogeneous heterochromous fibre.

If the to-be-detected yarn 6 is a heterogeneous yarn made from polypropylene fibre, polyester fibre or nylon fibre and so on, ultraviolet light irradiating on the to-be-detected yarn 6 may be excited to generate fluorescent light. A part of the fluorescent light may be propagated backward and received by the detector 3 through the light filter 5, while another part of the fluorescent light may be reflected by the reflector 5 together with the ultraviolet spectrum, then is filtered by the light filter 5 and then is projected onto the photosurface of the detector 3. Therefore, arrangement of the reflector 5 is advantageous to increasing the intensity of a fluorescence signal captured by the detector 3.

If the to-be-detected yarn 6 is common cotton yarn, the ultraviolet light irradiating on the to-be-detected yarn 6 may be reflected back by the to-be-detected yarn 6. The rest of the ultraviolet light irradiating on the reflector 5 is reflected back by the reflector, and after being filtered by the light filter 5, the reflected ultraviolet light irradiates on the photosurface of the detector 3.

The light intensity of the fluorescent light is lower than that of the ultraviolet light. If the yarn has heterogeneous yarn, the light intensity signal received by the detector 3 may be decreased. Therefore, using the rear-projection photodetection yarn clearing apparatus of the present disclosure, a weak signal caused by homochromatic hetero fibre or homogeneous heterochromous fibre in the yarn may be determined and captured, so that a circuit discrimination system emits signals of 0 and 1 to switch off homochromatic hetero fibre and homogeneous heterochromous fibre.

Furthermore, since the light intensity difference between the fluorescent light and the ultraviolet light is small, it is required the detector 3 having a high precision to determine and capture the fluorescence signal, which is demanding for the detector 3.

The detector 3 of the present disclosure is a PIN-type ultraviolet enhanced silicon photodiode. To quicken the response speed of the detector 3, the ultraviolet enhanced silicon photodiode is made from a high-resistivity N-type (111) silicon wafer having a resistivity of 3,000Ω·cm. The silicon wafer is 6 inches in size, one-side polished, and has a field oxide thickness of 1,000 nm. A side of the silicon wafer is implanted with boron having an implantation dose of $4 \times 10^{14}$ cm$^{-2}$~$5 \times 10^{14}$ cm$^{-2}$ and energy of 30 Kev to form a P-type area, another side of the silicon wafer is implanted with phosphorus having an implantation dose of $5 \times 10^{15}$ cm$^{-2}$ and energy of 100 Kev to form an N+ area, the P-type area of the silicon wafer is polished, and the N+ area of the silicon wafer is burnished. The oxide layer thickness of the polished P-type area and of the burnished N+ area is reduced to 50 nm~60 nm. The ultraviolet enhanced silicon photodiode is processed using a two-stage high and low temperature annealing process: first processed at a high temperature of 1,000° C. for 30 s, and then processed at a low temperature of 600° C. for 8-12 h. The finally manufactured ultraviolet enhanced silicon photodiode may have a photosurface area of 4 mm×4 mm, or 6.19 mm×6.425 mm, or other values desired by the user, a reverse breakdown voltage greater than 80V, and a junction capacitance Ct=0.106 nF. The ultraviolet enhanced silicon photodiode can begin to respond from 190 nm, and has a response peak of 720 nm. A light current about 0.10 A can be generated when irradiation of 1 W light is received at a wavelength of 200 nm. A light current about 0.065 A can be generated when irradiation of 1 W light is received at a wavelength of 390 nm. A light current about 0.36 A can be generated when irradiation of 1 W light is received at the response peak of 720 nm. At 25, a dark current measured at a reversed bias voltage of 1V is $10^{-10}$ A.

In the event that preparation raw materials are the same, Hamamatsu Corporation implants a side of an N-type silicon wafer with boron having an implantation dose of $1\times10^{15}$ $cm^{-2}$ and energy of 150 Kev, then implants another side of the N-type silicon wafer with phosphorus having an implantation dose of $1\times10^{15}$ $cm^{-2}$ and energy of 150 Kev, and then the N-type silicon wafer is processed at a temperature of 1,100° C. for 8-12 h. In this way, a S1266-8BQ silicon photodiode is finally manufactured, which has a junction capacitance of Ct=1.3 nF.

Figure 3:
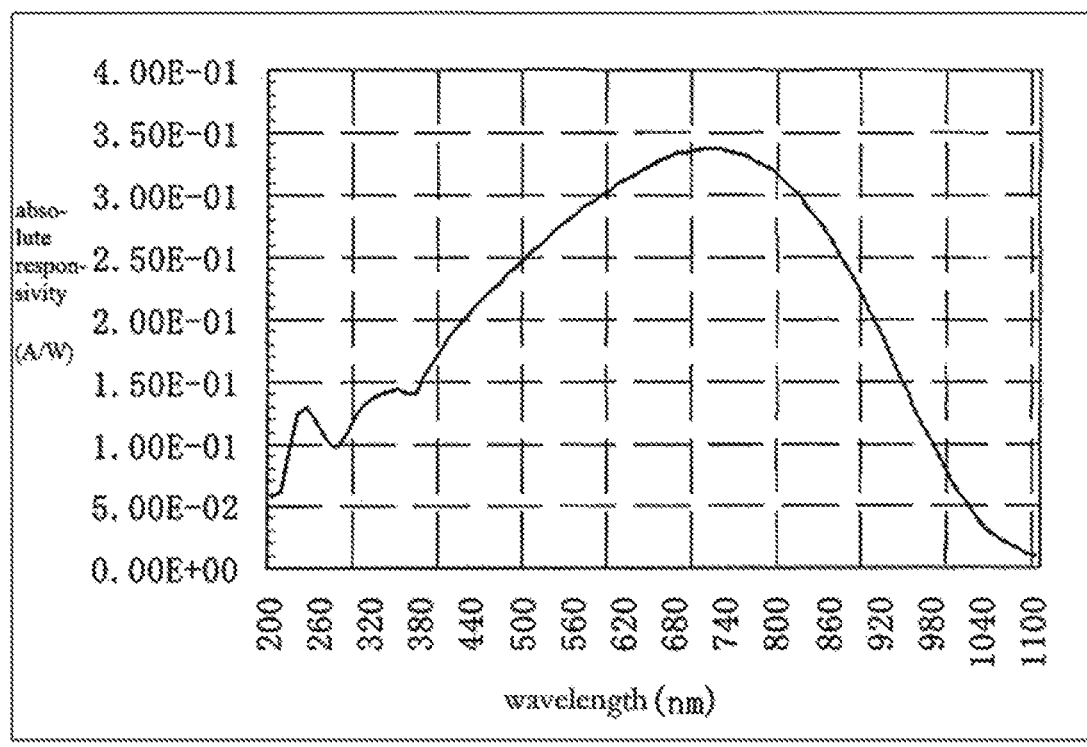
FIG. 3 is a response curve of the ultraviolet enhanced silicon photodiode of the present disclosure.

As can be known from the above comparison result, the response speed of the silicon photodiode of the present disclosure is increased by above ten times, so that it is possible that the yarn clearing apparatus can detect homochromatic hetero fibre and homogeneous heterochromous fibre according to the photodetection method. Specific effects of the silicon photodiode of the present disclosure have been tested by National Institute of Metrology, the certificate number is GXte2008-0317, and the test results are shown in FIG. 3.

Too much stray light into the detector 3 may cover a to-be-detected signal, which is disadvantageous to determining and capturing the fluorescence signal. The stray light irradiating into the middle cavity 14 from outside of the bracket 1 may be reflected by the reflector 5 out of the middle cavity 14, and thus does not directly irradiate on the photosurface of the detector 3, which is advantageous to eliminating the stray light. To enhance the effect of the reflector 5 in filtering stray light, a rear mirror surface of the reflector 5 is in parallel with the photosurface of the detector 3.

A front end face of the light emitting diode 2 in the present disclosure is flush with the front end face of the detector 5, so that light emitted from the light emitting diode 2 does not directly enter into the detector 5, but is filtered by the light filter 4 and then is propagated into the middle cavity 14.

An embodiment of the ultraviolet enhanced silicon photodiode of the present disclosure:

The specific structure of the ultraviolet enhanced silicon photodiode of the present disclosure is the same as that of the ultraviolet enhanced silicon photodiode in the embodiment of the rear-projection photodetection yarn clearing apparatus, and details may be referred to FIG. 2 and FIG. 3 and thus are omitted herein.

What is claimed is:

1. A rear-projection photodetection yarn clearing apparatus, comprising a light emitting diode and a detector arranged behind a to-be-detected yarn, and further comprising a reflector arranged in front of the to-be-detected yarn, wherein a front end face of the light emitting diode is flush with a photosurface of the detector, a light filter for capturing light rays having a waveband ranging from 330 nm to 470 nm is further arranged in front of the light emitting diode and the detector, a light-reflecting surface of the reflector is in parallel with the photosurface of the detector; the light emitting diode comprises an ultraviolet light emitting diode, the detector comprises an ultraviolet enhanced silicon photodiode, the ultraviolet enhanced silicon photodiode is made from a high-resistivity N-type (111) silicon wafer having a resistivity of 3,000Ω·cm and a field oxide thickness of 1,000 nm, a side of the silicon wafer is implanted with boron having an implantation dose of $4\times10^{14}$ $cm^{-2}$~$5\times10^{14}$ $cm^{-2}$ and energy of 30 Kev to form a P-type area, another side of the silicon wafer is implanted with phosphorus having an implantation dose of $5\times10^{15}$ $cm^{-2}$ and energy of 100 Kev to form an N+ area, the P-type area of the silicon wafer is polished, the N+ area of the silicon wafer is burnished, and both the P-type area and the N+ area have an oxide layer thickness of 50 nm~60 nm.

2. The rear-projection photodetection yarn clearing apparatus according to claim 1, wherein the ultraviolet enhanced silicon photodiode is processed using a two-stage high and low temperature annealing process: first processed at a high temperature of 1,000° C. for 30 s, and then processed at a low temperature of 600° C. for 8-12 h.

3. The rear-projection photodetection yarn clearing apparatus according to claim 2, wherein the light emitting diode is symmetrically arranged at a left side and a right side of the detector, a number of the light emitting diodes at either side is at least two, and the light emitting diodes at either side are uniformly distributed at intervals along upper and lower directions.

4. The rear-projection photodetection yarn clearing apparatus according to claim 2, wherein a shell of the light emitting diode comprises a frosting surface diverging light rays.

5. The rear-projection photodetection yarn clearing apparatus according to claim 1, wherein the detector is connected to a signal processing system comprising a signal receiving module, an amplifier module, a filter module, a shaper module and a comparison output module sequentially arranged.

6. The rear-projection photodetection yarn clearing apparatus according to claim 1, further comprising:
    a bracket, wherein the bracket includes a first interior side positioned in front, a second interior side positioned in the rear, and a third interior side positioned beneath, the first interior side, the second interior side and the third interior side cause the bracket to be concave, a concave-shaped middle cavity allows a to-be-detected yarn to pass through along a left direction and a right direction, the bracket is separated by the middle cavity into a front bracket and a rear bracket.

7. The rear-projection photodetection yarn clearing apparatus according to claim 6, wherein a cross section of the rear bracket is rectangle-shaped, and a middle portion of the rear bracket is provided with a rectangular through hole which is front-back penetrated through, and the through hole is internally provided with the detector, on the rear bracket, a left end and a right end of the through hole are respectively provided with mounting holes for mounting a light emitting diode, the mounting holes at either side are uniformly distributed at intervals along upper and lower directions, and the mounting holes at the left side and the right side of the rear bracket are bilaterally symmetrical, the left side and the right side of the rear bracket are respectively provided with light emitting diodes.

8. The rear-projection photodetection yarn clearing apparatus according to claim 7, wherein the light emitting diode is an ultraviolet light emitting diode that can emit light rays having a wavelength ranging from 340 nm to 405 nm, a front end of the light emitting diode and of the detector does not go beyond the second interior side, the second interior side is provided with the light filter for filtering heterochromatic light out and only allowing light rays whose wavelength ranges from 330 nm to 470 nm to pass through, and the first interior side is provided with the reflector.

9. The rear-projection photodetection yarn clearing apparatus according to claim 8, wherein after irradiating on the to-be-detected yarn in the middle cavity, ultraviolet light is reflected back by the reflector, the reflected ultraviolet light irradiates on the photosurface of the detector through the light filter, and the detector converts a received light signal into an electrical signal, after the electrical signal is processed by a signal processing system, a control signal is emitted to switch off hetero homochromatic fibre and homogeneous heterochromous fibre in the to-be-detected yarn.

10. An ultraviolet enhanced silicon photodiode, made from a high-resistivity N-type (111) silicon wafer having a resistivity of 3,000Ω·cm and a field oxide thickness of 1,000 nm, wherein a side of the silicon wafer is implanted with boron having an implantation dose of $4 \times 10^{14}$ cm$^{-2}$~$5 \times 10^{14}$ cm$^{-2}$ and energy of 30 Kev to form a P-type area, another side of the silicon wafer is implanted with phosphorus having an implantation dose of $5 \times 10^{15}$ cm$^{-2}$ and energy of 100 Kev to form an N+ area, the P-type area of the silicon wafer is polished, the N+ area of the silicon wafer is burnished, and both the P-type area and the N+ area have an oxide layer thickness of 50 nm~60 nm.

11. The ultraviolet enhanced silicon photodiode according to claim 10, wherein the ultraviolet enhanced silicon photodiode is processed using a two-stage high and low temperature annealing process: first processed at a high temperature of 1,000° C. for 30 s, and then processed at a low temperature of 600° C. for 8-12 h.

* * * * *